United States Patent [19]

Quaresima

[11] Patent Number: 5,715,030
[45] Date of Patent: Feb. 3, 1998

[54] ANTI-GLARE EYE SHIELD

[75] Inventor: James S. Quaresima, Hampton Bays, N.Y.

[73] Assignee: Vi-Zor Corp., Hampton Bays, N.Y.

[21] Appl. No.: 740,900

[22] Filed: Nov. 4, 1996

Related U.S. Application Data

[63] Continuation-in-part of Ser. No. 552,618, Nov. 3, 1995, Pat. No. 5,598,230.

[51] Int. Cl.$^6$ .............. G02C 7/10; G02C 9/00; G02C 1/00; A61F 9/00
[52] U.S. Cl. .............. 351/44; 351/47; 351/124; 351/158; 2/12
[58] Field of Search .............. 351/41, 44, 47, 351/142, 147, 158, 149; 2/12, 13, 446

[56] References Cited

U.S. PATENT DOCUMENTS

| | | | |
|---|---|---|---|
| D. 136,539 | 10/1943 | Jones | D29/18 |
| D. 164,304 | 8/1951 | Houston | D57/1 |
| D. 167,193 | 7/1952 | Bruce | D57/1 |
| D. 168,736 | 2/1953 | Cooper et al. | D57/1 |
| D. 169,130 | 3/1953 | Dieroff | D54/1 |
| D. 176,309 | 12/1955 | Clark | D57/1 |
| D. 204,023 | 3/1966 | Potts | D57/1 |
| D. 302,609 | 8/1989 | Wheeler | D29/18 |
| 1,255,430 | 2/1918 | King | 2/12 |
| 1,722,120 | 7/1929 | Wickland | 2/12 |
| 2,187,810 | 1/1940 | Rentz | 88/41 |
| 2,433,590 | 12/1947 | Barr | 2/12 |
| 2,530,881 | 11/1950 | Houston | 2/12 |
| 2,632,164 | 3/1953 | Hanford | 2/12 |
| 2,933,734 | 4/1960 | Glass | 2/9 |
| 3,225,459 | 12/1965 | Wilstein | 35/12 |
| 3,308,478 | 3/1967 | Tate | 2/12 |
| 3,330,051 | 7/1967 | Pambello | 35/12 |
| 4,057,852 | 11/1977 | Contant | 2/12 |
| 5,261,124 | 11/1993 | Day | 2/10 |

*Primary Examiner*—Huy Mai
*Attorney, Agent, or Firm*—Roylance, Abrams, Berdo & Goodman, L.L.P.

[57] ABSTRACT

An anti-glare eye shield particularly suitable for use by computer operators includes a hood portion to shield the user's eyes from overhead lighting as well as peripheral lighting, an adjustable shield, and a nose bridge support. The bottom face of the hood portion includes a plurality of recesses for selectively receiving a nose bridge support and the adjustable shield. The nose bridge support and adjustable shield are removably attached to the hood by inserting the members into the appropriate recess to accommodate the facial characteristics of the user. The eye shield is particularly suitable for limiting the field of view of the user to enable to user to focus on the computer screen and reduce the incidence of eyestrain and fatigue. The shield is dimensioned to be fit over the user's glasses without discomfort.

20 Claims, 3 Drawing Sheets

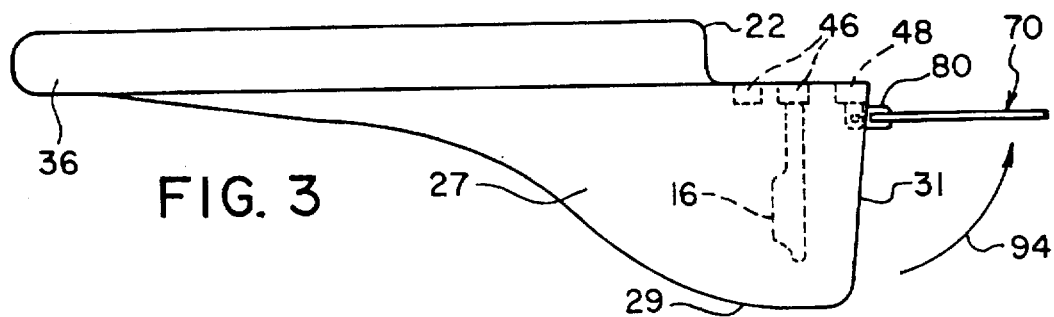
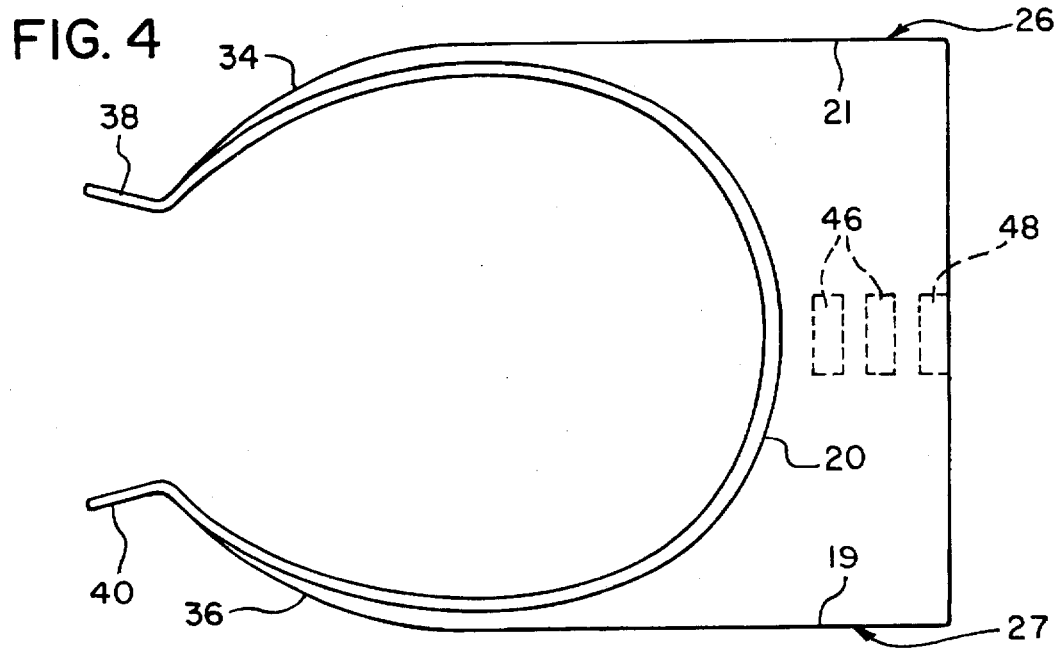
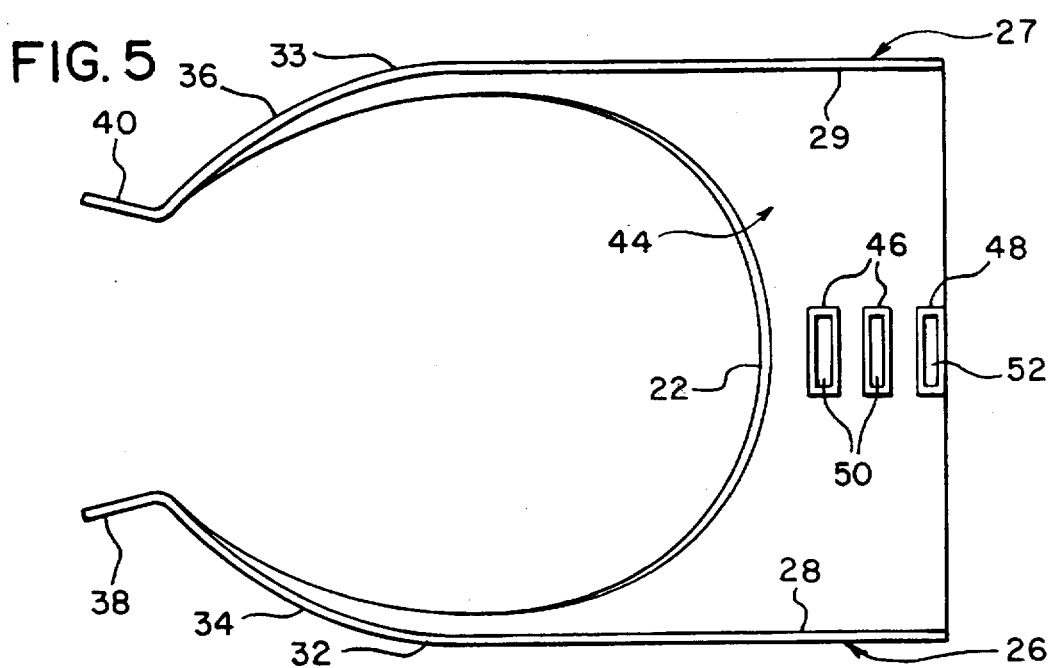

ANTI-GLARE EYE SHIELD

CROSS-REFERENCE TO RELATED APPLICATION

This application is a continuation-in-part application of U.S. application Ser. No. 08/552,618 filed Nov. 3, 1995, now U.S. Pat. No. 5,598,230.

FIELD OF THE INVENTION

The present invention is directed to an ergonomically designed anti-glare eye shield primarily for use by computer operators. More particularly, the invention is directed to an anti-glare eye shield having an adjustable nose support and adjustable UV eye shield to provide maximum comfort to the user.

BACKGROUND OF THE INVENTION

With the advent of computers in the office and at home has come many health problems which previously were either unknown or occurred only in few isolated cases. Daily use of computers has resulted in a variety of work-related injuries to the neck, head, arm and hand which are typically referred to as repetitive stress injuries. These injuries usually occur by performing repetitive movements or by being required to remain in a specific position for long periods of time.

Eye strain and fatigue are common problems associated with prolonged use of computers. The constant glare from the computer screens often result in eye strain, which can lead to severe headaches and other discomforts. Reflections on the computer screen from overhead lights also contribute to eye strain and fatigue. In addition, background and overhead lighting can produce glare in the computer operator's eyes which makes it difficult for the operator to focus on the computer monitor.

Numerous methods have been proposed in the past to reduce eye strain when using a computer for prolonged periods of time. These methods include such means as reducing the level of background and overhead lighting, consciously blinking frequently to keep the eyes moist and clean, maintaining regular breathing rates, and taking regular breaks. In the workplace, however, these methods are often impossible to achieve and are impractical to implement.

Numerous anti-glare eye shields and eye shades have been proposed for various purposes. For example, various eye shields have been proposed for drivers and pilots to reduce the glare from the sun or lights. Other eye shields have been proposed which serve as blinders to avoid distraction during various activities and for training exercises. Examples of these types of eye shields are disclosed in U.S. Pat. Nos. 2,933,734; 3,330,051; 3,308,498; 3,225,459 and 5,261,124. These devices do not provide adequate protection from glare and reflection from incidental light, as well as the glare from the computer terminal. Furthermore, these devices are typically bulky and uncomfortable to wear.

Numerous ergonomic products are currently available to reduce or minimize the discomfort associated with prolonged computer use. These devices are primarily directed to preventing carpal tunnel syndrome and muscle fatigue. However, these devices do not provide prevention of eye strain. Accordingly, there is a continuing need in the industry for a device for reducing eye strain caused by prolonged computer use.

SUMMARY OF THE INVENTION

A primary object of the invention is to provide an ergonomic eye shield for blocking the glare usually encountered by a computer operator.

Another object of the invention is to provide an eye shield having a removable and adjustable UV filter for blocking the user's eyes from UV radiation.

A further object of the invention is to provide a device for shielding distractions from the view of the operator.

Another object of the invention is to provide an eye shield to enable a computer operator to tunnel their view and focus their attention on the computer monitor, thereby reducing focus stress.

A further object of the invention is to provide an eye shield for reducing eye fatigue and eye strain caused by prolonged use of a computer.

Another object of the invention is to provide an eye shield having a UV filter with prescription lenses to reduce eye fatigue.

The objects of the invention are basically attained by providing an eye shield comprising a top portion having a first edge conforming to a wearer's forehead, a second edge opposite the first edge and a pair of side edges extending between the first and second edges; a side member coupled to each of the side edges and extending substantially perpendicular to the top portion; a pair of temple members coupled to each of the side members for engaging a wearer's head; a UV filter coupled to said top potion for shielding a wearer's eyes; a nose bridge support for supporting the shield; and a plurality of spaced apart coupling means on a bottom surface of the top portion for removably coupling with the nose bridge, each of the coupling means being positioned along an axis and spaced from the first edge for selectively spacing the nose bridge from the first edge.

The objects of the invention are further attained by providing an anti-glare eye shield comprising a substantially planar top portion having a first edge conforming to a wearer's forehead, a second edge opposite the first edge, and a pair of parallel side edges; first and second side portions extending from the side edges substantially perpendicular to the top portion, each of the side portions having a first curved end, wherein the curved end of each side portion forms a head encircling band; at least one raised collar portion extending from a bottom face of the top portion and having at least one recess therein proximate the first edge of the top portion; and a removable UV filter frictionally engaging the recess.

Other objects, advantages and salient features of the invention will become apparent from the following detailed description which, taken in conjunction with the annexed drawings, disclose preferred embodiments of the invention.

BRIEF DESCRIPTION OF THE DRAWINGS

Referring now to the drawings, which form a part of this original disclosure:

FIG. 3 is a side elevational view of the eye shield in one embodiment of the invention;

FIG. 4 is a top plan view of the eye shield;

FIG. 5 is a bottom plan view of the eye shield of FIG. 1;

DETAILED DESCRIPTION OF THE DRAWINGS

Figure 1:
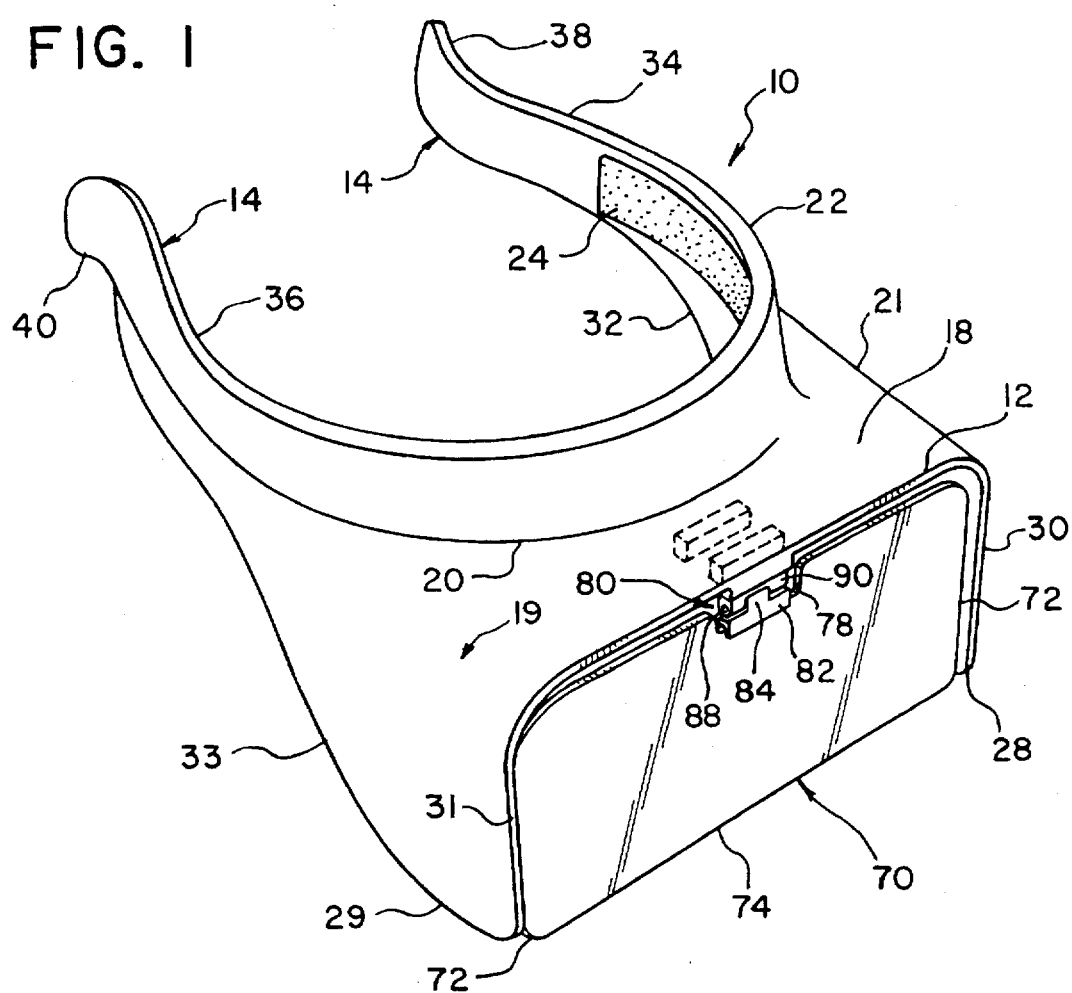
FIG. 1 is a top perspective view of the anti-glare eye shield in a first embodiment of the invention showing the shield and the UV filter of the shield.

The present invention is directed to an eye shield 10 particularly adapted to be worn by a computer operator to protect the operator from glare and reflection from the surrounding light. The eye shield 10 is an ergonomically designed device to shield the operator from distractions enabling the operator to focus their attention on the computer monitor and to protect the user from glare and UV light from the computer screen. The anti-glare eye shield 10 includes a hood portion 12, head gripping arms 14, a nose bridge support 16 and an adjustable shield 70. The hood portion 12 is designed to shield the operator's eyes from competing light sources, thereby tunneling the operator's view to the computer screen, thereby reducing eye strain and focus stress.

The hood portion 12 of the eye shield 10 includes a substantially planar top portion 18 having a curved first inner edge surface 20 shaped to conform to and rest against the forehead of the user. A depending lip 22 extends upwardly from the first edge 20 to define a smooth surface for contacting the user's forehead. The depending lip 22 preferably includes a soft padding or cushion material 24 to make the device more comfortable to wear. The soft padding material 24 can be an absorbent or non-absorbent foam pad or cloth material. In the embodiment illustrated, the depending lip 22 also has a concave shape conforming to the shape of inner edge 20 and is positioned in the approximate center of the top portion 18. In alternative embodiments, the lip 22 can extend along only a portion of the length of edge 20 to provide maximum contact with the forehead of the user.

Figure 2:
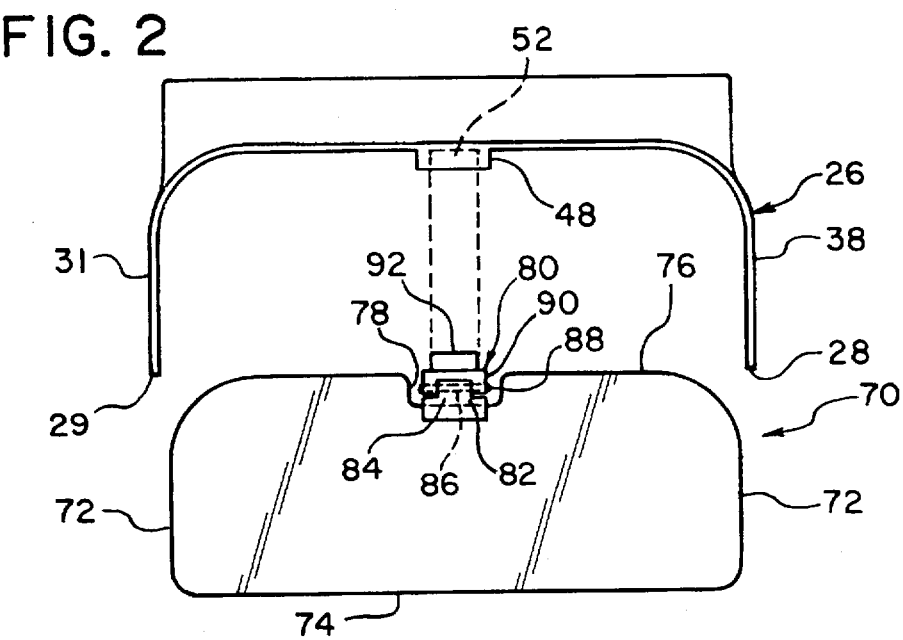
FIG. 2 is a front elevational view of the eye shield of FIG. 1.

The hood portion 12 also includes a pair of side members 26 and 27 extending substantially perpendicular to the top portion 18 along each of the opposite side edges 19 and 21, respectively, of the top portion 18. As shown in FIGS. 1–3, each side portion 26 and 27 has a lower edge 28 and 29, respectively, tapering toward the outer edge 30 and 31, respectively. The rear edge 32 and 33 of each side portion 26 and 29, respectively, tapers to form head gripping temple members 34 and 36, respectively. Each temple members 34 and 36 has a curved shape to grip the head of the user. Each temple member 34 and 36 includes a tab portion 38 and 40, respectively, extending outwardly from straps 34, 36. The members 34 and 36 are sufficiently resilient to spring outwardly to accommodate the user and frictionally grip the user's head comfortably. In the embodiment shown, the eye shield is a one-piece molded plastic member.

Figure 6:
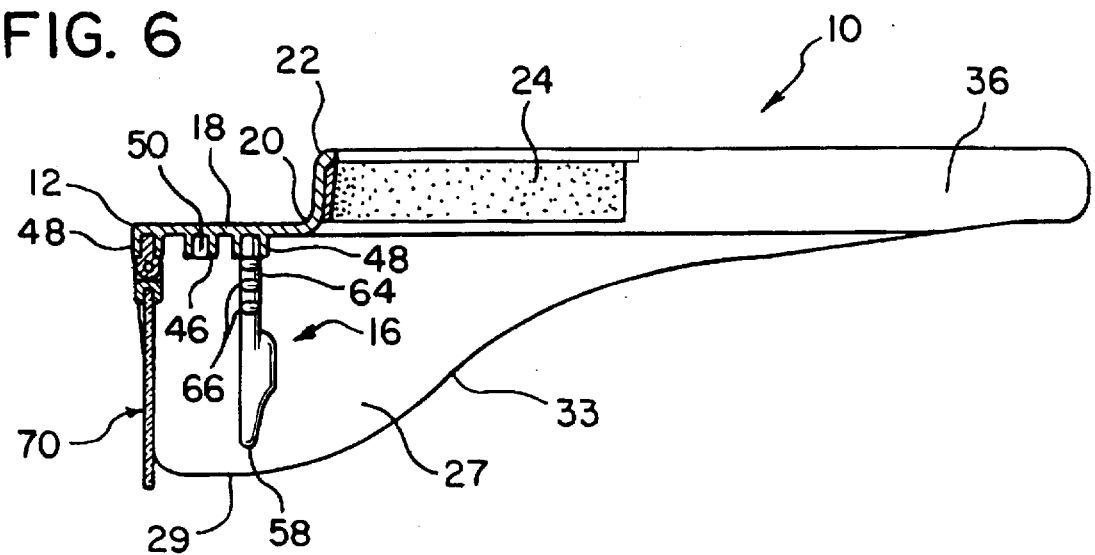
FIG. 6 is a cross-sectional view of the eye shield showing the nose bridge support and the adjustable UV filter.

As shown in FIGS. 3, 5 and 6, the bottom face 44 of top portion 18 includes first collar portion 46 and at least one second raised collar portion 48 forming a collar. The first raised portion 46 extends outwardly from the bottom face 44, and includes at least one recess 50. As shown, two recesses 50 are provided having an elongated substantially rectangular shape to form a plurality of slots. The recesses 50 are equally spaced apart in a row extending longitudinally from the inner edge 20 of the top portion 18. The second raised portion 48 is shown spaced from the first raised portion 46, and includes a single recess 52 having the shape of an elongated slot. The second raised portion 46 in the embodiment shown in FIG. 6 is adjacent the front edge of the top portion 18. In alternative embodiments, the raised portion can be spaced from the front edge.

The nose bridge 16 has a substantially elongated planar body portion 54 with a lower end 56 having a substantially Y-shape. The Y-shaped lower end 56 is defined by a pair of legs 58 diverging outwardly to form a smooth concave inner surface 60. Nose bridge 16 also includes an upper distal end 62 having a shape complementing the shape of the recesses 50 and 52. The upper end 62 of the nose bridge 16 frictionally engages the recesses to removably attach the nose bridge 16 to the top portion 18. A plurality of stop members 66 shown as detents extend from opposite sides of the nose bridge 16 to limit the depth of insertion of the nose bridge 16 into the recesses 50, 52. The stop members 52 engage the raised collar portions 46, 48 to assist in stabilizing the nose bridge. In this fashion, the position of the nose bridge 16 can be adjusted with respect to the first edge 20 of the top portion 18 to accommodate different users of the eye shield 10. In embodiments of the invention, the upper end 62 includes a resilient friction enhancing member 64 to assist in retaining the nose bridge 16 in the recesses 50 and 52. The friction enhancing member 64 can be a resilient rubber-like material or padding. The nose bridge 16 fits securely within the recesses 50 and 52 while allowing some side-to-side swinging adjustment to allow the device 10 to fit comfortably.

In embodiments of the invention, the nose bridge support 16 includes a plurality of frangible lines 66 extending across the body portion 54. In this manner, the length of the body portion 54 can be shortened by breaking the body portion along the frangible lines 66, and thus shortening the nose bridge 16 to accommodate the particular needs of the user.

Referring to FIGS. 1–3, a tinted shield or shade 70 is removably attached to the bottom surface of the hood portion 12 in front of the user's eyes. The tinted material can be, for example, a standard tinted transparent material, such as plastic or glass, used for manufacturing sunglasses. The amount of tinting in the shield can vary, depending on the intended use of the device. In preferred embodiments of the invention, the shield 70 is an ultraviolet light filter as used in the eyewear industry capable of blocking UV light and protecting the user from excessive UV light. The shield 70 is preferably made of plastic or other lightweight material.

Referring to FIGS. 1–3, shield 70 is a substantially flat member of substantially transparent material. As discussed above, the shield 70 is preferably tinted or opaque to reduce the glare. Shield 70 is shaped to conform to the front edge opening of the eye shield 12 as shown in FIGS. 1 and 2. As shown, shield 70 has substantially straight side edges 72 conforming to side portions 26, a straight bottom edge 74 and a top edge 76 conforming to top portion 18. A recessed portion 78 is formed in top edge 76 for coupling to a hinge assembly 80.

Hinge assembly 80 as shown in FIGS. 1 and 2 includes a first hinge member 82 coupled to the shield 70 by any suitable means such as by adhesively bonding or by a mechanical fastener. The first hinge member 82 includes an upward extension 84 having bore 86 for receiving a hinge pin 88. A second hinge member 90 is pivotally coupled to the first hinge portion by the pin 88. The second hinge member 90 includes a leg 92 dimensioned to frictionally engage the recess in the top portion 18. As shown in FIG. 3, the shield 70 is mounted in the eye shield and is pivotable upward to an inoperative position when not in use in the direction of arrow 94.

Figure 7:
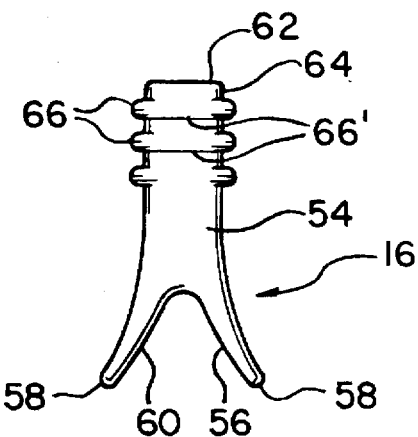
FIG. 7 is a front elevational view of the nose bridge support.
Figure 8:
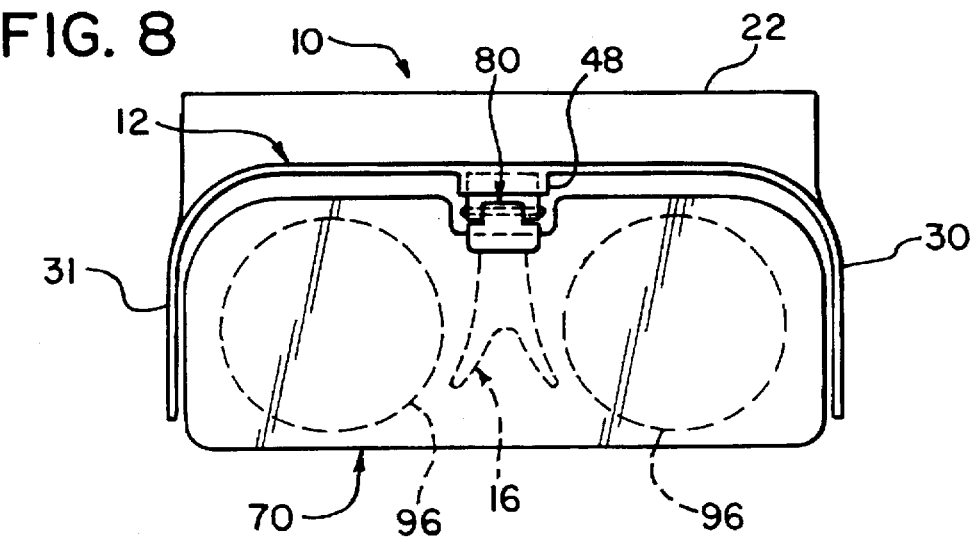
FIG. 8 is a front elevational view of the eye shield in a further embodiment of the invention.

In a further embodiment illustrated in FIG. 7, the shield 70 includes prescription lens area 96 for correcting the vision of the user or for magnifying an object being viewed. The shield 70 is adaptable for various prescription values to accommodate the user. The shield 70 is removable from eye shield 12 so that the shield 70 can be easily replaced or removed when not in use. The shield 70 can be tinted or contain a UV blocking agent to filter the light reaching the user's eyes.

In use, the straps 34 and 36 form a head encircling band to fit the head of the user. The nose bridge 16 is then placed in the appropriate recess 50 or 52 so that the lower end 56 of the nose bridge contacts the nose of the user to support the top portion 18 of the eye shield. If necessary, the length of the nose bridge can be adjusted to accommodate the needs of the user to properly support the eye shield. The eye shield 70 is then inserted into the recess 52.

The top portion 18 and side portions 26 are dimensioned to shield the user's eyes from glare and reflected light in the working environment. In particular, the eye shield 10 is dimensioned to be able to block overhead lighting which may interfere with the ability of the user to focus on the computer screen. The side portions 26 also block the user's view of any distracting activity occurring around the worksite to enable the user to properly focus on the computer screen. In preferred embodiments, the inner surfaces of the top portion 18 and side portions 26 and 27 have a non-reflective surface to further reduce distractions by reflected light.

The eye shield 10 of the invention is able to be comfortably worn by the user and is able to accommodate a variety of facial features. The eye shield is also able to be worn by the user without interfering with the user's eyeglasses since the shield 10 is dimensioned to fit over the user's glasses and the nose bridge 16 can be positioned to avoid interfering with the glasses. The eye shield is particularly suitable for people wearing glasses to reduce peripheral glare and to reduce the amount of reflected light on the front and rear surfaces of the lenses.

In embodiments of the invention, the eye shield is an integrally molded article made of flexible plastic but rigid enough to retain its shape. The hood 12 and head encircling band are preferably formed as a single piece. Typically, the eye shield is made using standard injection molded techniques as known in the art.

The eye shield 10 is primarily directed for use by people who spend large amounts of time at computer terminals to minimize the incidence of eye strain and fatigue. The shield can have alternative uses, such as, for example, training exercises where limiting the field of view is desired.

While advantageous embodiments have been chosen to illustrate the invention, it will be understood by those skilled in the art that various changes and modifications can be made therein without departing from the scope of the invention as defined in the appended claims.

What is claimed is:

1. An anti-glare eye shield comprising
   a top portion having a first edge conforming to a wearer's forehead, a second edge opposite said first edge and a pair of side edges extending between said first and second edges;
   a side member coupled to each of said side edges and extending downwardly substantially perpendicular to said top portion;
   a pair of resilient temple gripping members coupled to each of said side members for gripping a wearer's head;
   a UV filter for shielding a user's eyes;
   a nose bridge support for supporting said shield; and
   a plurality of coupling means on a bottom surface of said top portion for removably coupling with said nose bridge and said UV filter, each said coupling means being positioned along an axis and spaced from said first edge for selectively spacing said nose bridge from said first edge.

2. The eye shield of claim 1, wherein said top portion is a substantially flat planar body.

3. The eye shield of claim 1, wherein said coupling means on said top portion comprises a plurality of spaced-apart recesses, for receiving said nose bridge and said UV filter.

4. The eye shield of claim 3, wherein said top portion includes a collar surrounding said recesses.

5. The eye shield of claim 3, comprising a projecting portion on said bottom surface of said top portion and said recesses being formed in said projecting portion.

6. The eye shield of claim 1, wherein said nose bridge includes a substantially Y-shaped nose engaging portion and an elongated body portion having a distal end for coupling with said coupling means on said top portion.

7. The eye shield of claim 6, wherein said distal end of said nose piece includes a friction enhancing means.

8. The eye shield of claim 7, wherein said friction enhancing means is a resilient member.

9. The eye shield of claim 1, wherein said top, side and temple gripping members are integrally formed and made of plastic.

10. The eye shield of claim 1, wherein said UV filter includes a pivotal hinge member removably coupled to one of said coupling means on said top portion for pivotally coupling said UV filter in said first position shielding a user's eyes to a second inoperative position.

11. An anti-glare eye shield comprising:
    a substantially planar top portion having a first edge conforming to a wearer's forehead, a second edge opposite said first edge, and a pair of parallel side edges;
    first and second side portions extending from said side edges substantially perpendicular to said top portion, each said side portion having a resilient temple gripping member, wherein said temple gripping member forms a head encircling member;
    a first raised collar portion extending from a bottom face of said top portion and having at least one recess therein proximate the first edge of said top portion and at least one second collar portion having a recess spaced from the first edge; and
    a substantially transparent shield member having a leg for frictionally engaging said recess and removably coupling said shield member to said eye shield.

12. The eye shield of claim 11, wherein said bottom face of said top portion comprises a second raised collar portion spaced from said first raised collar portion.

13. The eye shield of claim 11, wherein said recesses are a plurality of elongated slots.

14. The eye shield of claim 13, further comprising a nose bridge support frictionally engaging one of said recesses wherein an upper end of said nose bridge has a substantially rectangular cross-section complementing the dimension of said elongated slots.

15. The eye shield of claim 12, wherein said upper end of said nose bridge comprises a resilient friction enhancing member.

16. The eye shield of claim 11, wherein curved ends of said side portions include a coupling means.

17. The eye shield of claim 16, wherein said transparent shield comprises a pivotal hinge member removably coupled to said recess in said first collar, and wherein said transparent shield is pivotal from a first position shielding a user's eyes to a second inoperative position.

18. The eye shield of claim 11, wherein said transparent shield is a UV filter.

19. The eye shield of claim 11, wherein said transparent shield is tinted.

20. The eye shield of claim 11, wherein said transparent shield includes a corrective lens.

* * * * *